(12) United States Patent
Hamama

(10) Patent No.: US 6,557,557 B2
(45) Date of Patent: May 6, 2003

(54) PATIENT MONITORING DEVICE WITH NON-SLIP STRAP

(76) Inventor: Naeil J. Hamama, 23260 Halsted Rd., #101, Farmington Hills, MI (US) 48335

( * ) Notice: Subject to any disclaimer, the term of this patent is extended or adjusted under 35 U.S.C. 154(b) by 0 days.

(21) Appl. No.: 09/727,868

(22) Filed: Dec. 4, 2000

(65) Prior Publication Data

US 2002/0068883 A1 Jun. 6, 2002

(51) Int. Cl.⁷ .................................................. A61F 5/37
(52) U.S. Cl. .......................... 128/876; 128/877; 604/179
(58) Field of Search ................................. 128/869, 876, 128/846, 877, 878, 879; 602/5, 20, 21, 23; 604/174, 179

(56) References Cited

U.S. PATENT DOCUMENTS

| | | | | |
|---|---|---|---|---|
| 4,692,364 A | * | 9/1987 | Altus | 428/85 |
| 5,209,482 A | * | 5/1993 | Hopfer | 273/187.2 |
| 5,292,044 A | * | 3/1994 | Reimers | 224/264 |
| 5,411,484 A | * | 5/1995 | Shattuck | 604/179 |
| 5,433,359 A | * | 7/1995 | Flowers | 224/222 |
| 5,737,771 A | * | 4/1998 | Aanonsen | 2/16 |
| 6,015,132 A | * | 1/2000 | Belle | 248/683 |
| 6,193,012 B1 | * | 2/2001 | Olivas | 224/257 |
| 6,467,661 B1 | * | 10/2002 | Mistretta | 224/264 |

FOREIGN PATENT DOCUMENTS

GB            2309487        *  7/1997

* cited by examiner

Primary Examiner—Michael A. Brown
(74) Attorney, Agent, or Firm—Charles W. Chandler

(57) ABSTRACT

A non-slip strap that can be connected to a patient monitoring device to resist movement of the device when the patient moves beyond a predetermined distance in his bed.

8 Claims, 1 Drawing Sheet

PATIENT MONITORING DEVICE WITH NON-SLIP STRAP

BACKGROUND AND SUMMARY OF THE INVENTION

This invention is related to a non-slip strap that can be wrapped around a smooth article, and more particularly to such a strap that is connected to a patient monitoring device to resist movement of the device when the patient moves beyond a predetermined distance.

Patient monitoring devices are commonly used in a home, a residential care facility or in hospitals to monitor the movements of a patient.

In one type of patient monitoring device, a pin is connected to a monitor housing by a cord fastened to the patient. The cord has a fixed length. If the patient moves beyond that length, the monitoring device is activated to sound an alarm. The cord is connected to a patient, such as to the patient's clothing, so that if the patient slumps from a wheelchair onto the floor, or moving over the edge of a bed, the monitoring device generates the alarm.

The alarm is commonly mounted on the wheelchair or a bed rail, by means of a flexible fabric strap that is wrapped around the rail. The ends of the strap are connected together by releasable fabric fasteners, such as well-known Velcro fasteners, which comprise a first patch of a flexible hook material and a second patch of a flexible loop material.

A problem arises in some cases because the conventional strap tends to slide along the rail when the patient moves so as to make the flexible cord taut. The taut cord pulls the strap and the alarm along the rail rather than separating the activating pin from the alarm housing.

The broad purpose of the present invention is to provide a non-slip strap that may be wrapped around an object having a smooth surface. In the preferred embodiment, the strap comprises an elongated fabric band. A rubber-like, non-slip material is fastened along a portion of the length of on one side of the band. The remainder of the same side of the band has fabric fastener hooks.

The opposite side of the strap is completely covered with fabric fastener loops. When the strap is wrapped around an elongated object, one side of the strap fastens tot he opposite side of the strap and made sufficiently snug on the object that the non-slip material prevents the strap from sliding along the object, such as a bed rail. The strap can be used either to connect one object to an elongated support, or to wrap several articles together. The strap can be used on wheelchairs, regular chairs, a couch, a bench or other smooth surface supports. It can be used in other non-health care industries. It can be made in any desirable shape or length.

Another object of the invention is to provide a patient monitoring device that is attached to such a strap to prevent the patient monitoring device from being pulled along a bed rail when the activating cord is rendered taut by patient movement.

Still further objects and advantages of the invention will become readily apparent to those skilled in the art to which the invention pertains upon reference to the following detailed description.

DESCRIPTION OF THE DRAWING

The description refers to the accompanying drawing in which like reference characters refer to like parts throughout the several views, and in which.

DESCRIPTION OF THE PREFERRED EMBODIMENT

Figure 1:
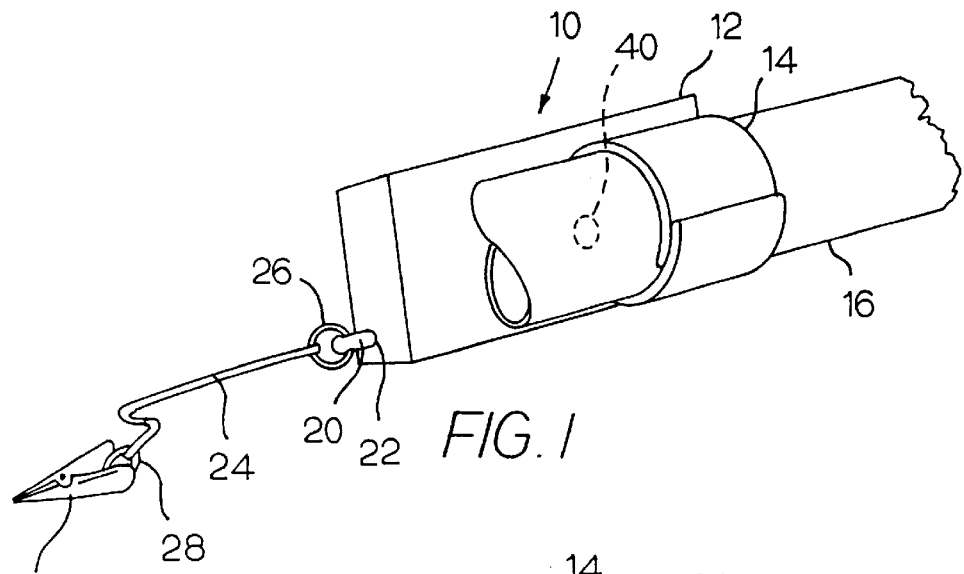
FIG. 1 is a perspective, fragmentary view of a patient monitoring device mounted on a bed rail employing a strap illustrating the invention.

Referring to the drawing, a preferred patient monitoring apparatus, illustrated at 10, comprises a patient monitoring device 12 mounted by a preferred strap 14 onto a bed rail 16.

Patient monitoring device 12 is typical of several similar monitoring devices available on the market. For illustrative purposes, device 12 is marketed under the mark "The Stat Alert 1" available from Alert One Safety Inc. The monitoring device comprises a housing 18 having a built-in alarm that is activated when a pin 20 is separated from an opening 22 in the housing.

An elongated flexible cord 24 has one end connected to pin 20 by a ring 26. The opposite end of cord 24 is connected by a ring 28 to a spring-loaded alligator clip 30 that may be attached to the patient's clothing. When the patient moves a predetermined distance beyond device 12, cord 24 is rendered taut and then pulls pin 20 from housing 18 to trigger the alarm.

Figure 2:
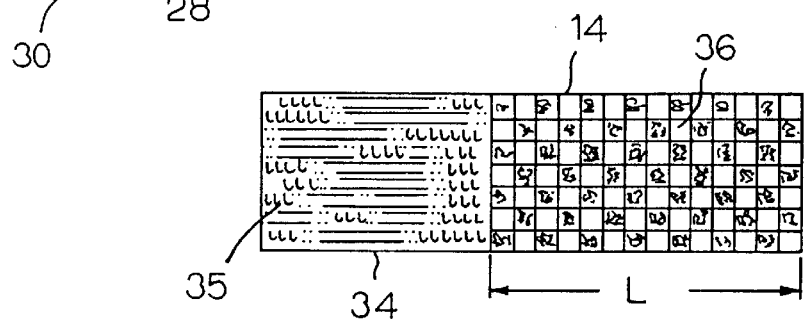
FIG. 2 is a view of one side of the strap.
Figure 3:
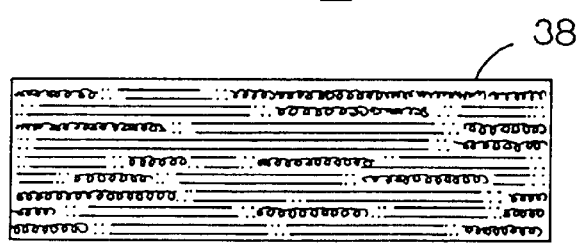
FIG. 3 is a view of the opposite side of the strap.
Figure 4:
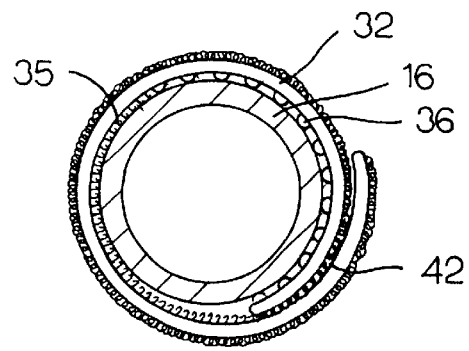
FIG. 4 is a view of the strap coiled into a loop.

Referring to FIGS. 2–4, strap 14 comprises an elongated flexible fabric band 32 having a length that is greater than the circumference of bed rail 16 so that when the band is wrapped the rail, one end overlaps the other end. One side of the band, for illustrative purposes, is completely covered at area 34, about one-half the length of the band, with fabric hook fasteners 35 of the type commonly known under the Velcro name. The remainder of the same side of the band is covered with a rubber-like non-slip material 36 having a knobbed pattern that covers the entire surface of the second end of the band.

Preferably the length "L" of the band, covered by the non-slip, raised pattern, is sufficient to encircle a major portion of the bed rail, however, it is not necessary that it cover the entire circumference of the bed rail.

The opposite side of the band as illustrated in FIG. 3, is entirely covered with fabric fastener loop material 38, which is also sold under the Velcro name. Loop material 38 is releasably engageable with hook fasteners 35.

The strap is attached to the monitoring device housing 18 by any suitable means, such as by one or more rivets 40, as shown in FIG. 1.

In use, the strap is wrapped around an elongated object, such as bed rail 16, with the surface of non-slip material 36 in contact with the bed rail. The two ends of the strap are then overlapped and connected together with the hook fasteners on one side of the strap engaging the loop fasteners on the opposite side of the strap, as illustrated at 42 in FIG. 4. The strap is snugly wrapped around the bed rail. The arrangement is such that when flexible cord 24 is rendered taut by movement of the patient, the cord imposes a force along the rail which is frictionally resisted by the rubber-like material, preventing the patient monitoring device from sliding along the rail. The taut cord causes pin 20 to separate from opening 22, thus triggering an alarm.

It is to be understood that other forms of non-slip rubber-like material can be employed with different patterns. Further, the strap may be attached by means other than rivets to the monitoring device, such as by using a suitable adhesive. Further, the strap may be employed on other types of monitoring devices, which employ a flexible cord, and imposes a force of the monitoring device along the bed rail. Further, the length of the strap may be any suitable length to accommodate the circumference of the bed rail or tool handle.

Having described my invention, I claim:

1. A patient monitoring apparatus comprising the combination of:

a patient monitoring device having an alarm;

a flexible member having a first end connected to the patient monitoring device so as to be separated therefrom at such times as the flexible member is disposed in a taut condition, whereby the patient monitoring device is activated to generate an alarm, the flexible member having a second end having means for connecting the flexible member to a patient such that the first end of the flexible member is disposed in a taut condition when the patient moves beyond a predetermined distance from the patient monitoring device;

a flexible strap comprising:

an elongated fabric band having a first side and an opposite, second side;

a non-slip pattern in the nature of a flexible elastomeric material mounted on the first side of the flexible band;

a first fabric fastener material mounted on the first side of the flexible band adjacent a first end thereof;

a second fabric fastener material mounted on the second side of the band adjacent a second end thereof;

means for fastening the band to the patient monitoring device;

the first fabric fastener material being releasably engageable with the second fabric fastener material whereby the strap may be snugly wrapped around an elongated annular surface with the non-slip pattern in contact therewith, and the first fastener material engaged with the second fastener material so the strap resists a force along the annular surface that is sufficient to separate the flexible member from the patient monitoring device.

2. A combination as defined in claim 1, in which the first fabric fastener material comprises a plurality of flexible fabric hooks, and the second fabric fastener material comprises a plurality of flexible fabric loops releasably engageable with the fabric hooks.

3. A combination as defined in claim 1, in which the non-slip pattern extends from the first end of the band toward the second end of the band and has a length sufficient to cover a portion of the circumferential surface of the annular surface.

4. A combination as defined in claim 1, in which the band has an overall length that is greater than the circumference of the annular surface whereby the first end of the band may be overlapped with the second end of the band.

5. A unitary non-slip strap, comprising:

an elongated, unitary, planar fabric band having a first side and a second side, a first end and a second end;

a non-slip pattern in the nature of a flexible elastomeric material mounted on one of said sides adjacent the first end of the fabric band;

a first releasable fastener structure attached on the opposite side of the elastomeric material in a back-to-back relationship thereto;

a second releasable fastener structure attached to the same side of the fabric band as the elastomeric material and back-to-back with the first fastener structure adjacent both said first end and said second end of the band;

the first releasable fastener structure being releasably engageable with the second releasable fastener structure when the first side of the band is pressed into engagement with the second side of the band to form a loop; and whereby the strap may be snugly wrapped around an object with the non-slip pattern in contact with said object, and the first fastener structure on said first side of the fabric band being releasably engaged with the second fastener structure on the second side of the band to resist a slidable motion of the band with respect to an object.

6. A non-slip strap as defined in claim 5, in which one of said fabric fastener structures comprises a plurality of flexible fabric loops, and the second of said fabric fastener structures comprises a plurality of fabric hooks releasably engageable with the fabric loops.

7. A unitary non-slip strip, as defined in claim 5, in which the non-slip pattern extends from the first end of the band toward the second end of the band and has a length sufficient to cover a portion of the circumferential surface of an annular surface.

8. A unitary non-slip strap as defined in claim 5, in which the first fastener structure comprises a plurality of flexible fabric hooks, and the second fastener structure comprises a plurality of flexible fabric loops releasably engageable with the fabric hooks.

* * * * *